(12) United States Patent
Batchelor et al.

(10) Patent No.: US 10,779,878 B2
(45) Date of Patent: Sep. 22, 2020

(54) THERMAL CONTROL DEVICES FOR ELECTROSURGICAL INSTRUMENTS

(71) Applicant: GYRUS ACMI, INC., Southborough, MA (US)

(72) Inventors: Kester J. Batchelor, Mound, MN (US); Huisun Wang, N Maple Grove, MN (US); Jeffrey James Nelson, Maple Grove, MN (US); Cristian Spanu, North Olmsted, OH (US); Nikhil M. Murdeshwar, Maple Grove, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 133 days.

(21) Appl. No.: 15/775,959

(22) PCT Filed: Nov. 25, 2015

(86) PCT No.: PCT/US2015/062717
§ 371 (c)(1),
(2) Date: May 14, 2018

(87) PCT Pub. No.: WO2017/091228
PCT Pub. Date: Jun. 1, 2017

(65) Prior Publication Data
US 2018/0325578 A1    Nov. 15, 2018

(51) Int. Cl.
*A61B 18/14* (2006.01)
*A61B 18/16* (2006.01)
(Continued)

(52) U.S. Cl.
CPC .......... *A61B 18/1442* (2013.01); *A61B 18/14* (2013.01); *A61B 18/16* (2013.01);
(Continued)

(58) Field of Classification Search
CPC ..... A61B 18/14; A61B 18/1442; A61B 18/16; A61B 2018/00005; A61B 2018/00023;
(Continued)

(56) References Cited

U.S. PATENT DOCUMENTS

| | | | |
|---|---|---|---|
| 4,674,498 A | 6/1987 | Stasz | |
| 4,850,353 A | 7/1989 | Stasz et al. | |

(Continued)

FOREIGN PATENT DOCUMENTS

| | | |
|---|---|---|
| CN | 1209047 | 2/1999 |
| CN | 203354640 | 12/2013 |

(Continued)

OTHER PUBLICATIONS

Japanese Office Action for Japanese Patent Application No. 2018-526908, dated May 13, 2019.

(Continued)

*Primary Examiner* — Michael F Peffley
(74) *Attorney, Agent, or Firm* — Schwegman Lundberg & Woessner, P.A.

(57) ABSTRACT

An effector includes a tubular body having a proximal end and a distal end. The effector includes a plug or closure at the distal end of the tubular body; an active electrode at the distal end of the body; an insulator on the body; and one or more return electrodes on the insulator. The body dissipates heat generated by the one or more return electrodes from the distal end of the body to the proximal end of the body.

20 Claims, 2 Drawing Sheets

(51) Int. Cl.
*A61B 18/00* (2006.01)
*A61B 18/12* (2006.01)
(52) U.S. Cl.
CPC .............. *A61B 2018/00005* (2013.01); *A61B 2018/00023* (2013.01); *A61B 2018/00083* (2013.01); *A61B 2018/00095* (2013.01); *A61B 2018/124* (2013.01); *A61B 2018/1412* (2013.01); *A61B 2018/1467* (2013.01); *A61B 2018/162* (2013.01); *A61B 2018/165* (2013.01)
(58) Field of Classification Search
CPC ........... A61B 2018/00083; A61B 2018/00095; A61B 2018/124; A61B 2018/1412; A61B 2018/1467; A61B 2018/162; A61B 2018/165
See application file for complete search history.

(56) References Cited

U.S. PATENT DOCUMENTS

| | | | |
|---|---|---|---|
| 4,862,890 A | 9/1989 | Stasz et al. | |
| 4,958,539 A | 9/1990 | Stasz et al. | |
| 6,503,248 B1 * | 1/2003 | Levine | A61B 18/1402 606/45 |
| 6,733,501 B2 | 5/2004 | Levine | |
| 6,832,998 B2 | 12/2004 | Goble | |
| 6,929,645 B2 | 8/2005 | Battles et al. | |
| 6,942,662 B2 * | 9/2005 | Goble | A61B 18/14 606/48 |
| 7,147,637 B2 | 12/2006 | Goble | |
| 8,100,894 B2 * | 1/2012 | Mucko | A61B 18/1442 606/27 |
| 2003/0125732 A1 | 7/2003 | Goble | |
| 2003/0130658 A1 | 7/2003 | Goble et al. | |
| 2004/0176761 A1 | 9/2004 | Desinger | |
| 2005/0283149 A1 | 12/2005 | Thorne et al. | |
| 2006/0264929 A1 | 11/2006 | Goble et al. | |
| 2009/0118732 A1 | 5/2009 | Desinger | |
| 2010/0152726 A1 | 1/2010 | Cadouri et al. | |
| 2011/0202057 A1 | 8/2011 | Thorne et al. | |
| 2011/0306968 A1 | 12/2011 | Beckman et al. | |
| 2014/0276796 A1 | 9/2014 | Batchelor et al. | |
| 2014/0276800 A1 | 9/2014 | Batchelor et al. | |
| 2015/0282873 A1 * | 10/2015 | Batchelor | A61B 18/1445 606/42 |

FOREIGN PATENT DOCUMENTS

| | | |
|---|---|---|
| CN | 108430364 A | 8/2018 |
| EP | 0455321 A1 | 11/1991 |
| EP | 1691705 A1 | 8/2006 |
| EP | 3364902 A1 | 8/2018 |
| JP | H4-227249 A | 8/1992 |
| JP | 4080827 B2 | 4/2003 |
| JP | 2005-512726 A | 5/2005 |
| JP | 2008-501485 A | 1/2008 |
| JP | 2009-202001 A | 9/2009 |
| JP | 2010-536398 A | 12/2010 |
| JP | 2019502431 A | 1/2019 |
| WO | WO-2017091228 A1 | 6/2017 |

OTHER PUBLICATIONS

International Search Report and Written Opinion for International Application PCT/US2015/062717 dated Jul. 28, 2016.
"European Application Serial No. 15813181.3, Communication Pursuant to Article 94(3) EPC dated Oct. 24, 2019", 6 pgs.
"International Application Serial No. PCT/US2015/062717, International Preliminary Report on Patentability dated Jun. 7, 2018", 8 pgs.
"Japanese Application Serial No. 2018-526908, Office Action dated Sep. 3, 2019", w/ English translation, 8 pgs.
"European Application Serial No. 15813181.3, Response filed Feb. 21, 2020 to Communication Pursuant to Article 94(3) EPC dated Oct. 24, 2019", 9 pgs.
"Japanese Application Serial No. 2018-526908, Notification of Reasons for Refusal dated May 21, 2019", 14 pgs.
"Japanese Application Serial No. 2018-526908, Response filed Jan. 6, 2020 to Office Action dated Sep. 3, 2019", w/ English Claims, 10 pgs.
"Japanese Application Serial No. 2018-526908, Response filed Aug. 16, 2019 to Office Action dated May 13, 2019", with English translation of claims, 8 pgs.
"Japanese Application Serial No. 2020-000204, Amendment filed Feb. 3, 2020", with English translation of claims, 5 pgs.
"Chinese Application Serial No. 201580085462.0, Office Action dated Apr. 27, 2020", w English Translation, 20 pgs.

\* cited by examiner

THERMAL CONTROL DEVICES FOR ELECTROSURGICAL INSTRUMENTS

FIELD

These teachings relate generally to medical instruments, and more particularly to devices for controlling heat in electrosurgical instruments.

BACKGROUND

Some electrosurgical instruments include an effector having one or more active electrodes and one or more return electrodes. The electrodes may be configured to apply energy to an object or anatomical feature to treat and/or otherwise effect the object or anatomical feature. For example, the applied energy can be used to cut, coagulate, seal, weld, dissect, and/or fulgurate an object or anatomical feature such as a vessel, tissue, artery, vein, organ, skin, the like, or a combination thereof. During use, the one or more return electrodes may become hotter and hotter, which may cause the object or anatomical feature to burn or stick to the effector or to the one or more electrodes. Such burning or sticking may increase the amount of time required to perform the medical procedure, may increase bleeding and/or tissue damage, or a combination thereof. Moreover, the increased temperature or heat at the return electrodes may cause the return electrodes to become the active electrodes, supplying a diffused or unintended effect. Equally, this additional heating may also cause arcing between electrodes due to increased energy in the area, particularly with bipolar cutting devices, potentially leading to a coagulating effect.

Some attempts have been made to thermally control and/or cool the return electrodes. For example, the size of the return electrodes have been increased to help dissipate heat from the return electrodes; however, incorporating larger electrodes undesirably increases the section size and weight of the effector or medical instrument, which is less than ideal for laparoscopic or minimally invasive procedures. Other attempts include incorporating individual fluid cooling, heat pipes, and/or heat tubes for each individual return electrode. However, incorporating individual fluid cooling, heat pipes, and/or heat tubes for each return electrode may also undesirably is the size, weight, and/or cost of the effector or medical instrument. Some electrosurgical instruments are disclosed in U.S. Patent Application Publication Numbers: 2003/0125732, 2006/0264929, 2014/0276804, 2014/0276786, 2014/0276799, 2014/0276800, 2014/0276772, 2014/0276795, 2014/0276797, 2014/0276795, 2014/0276796, 2014/027679, 2014/0276798, 2014/0276794, 2014/0276785, and 2015/0282873, and in U.S. Pat. Nos. 6,942,662, 6,832,998, 4,674,498, 4,850,353, 4,862,890, and 4,958,539—the disclosures of which, including all corresponding priority documents for these disclosures, are all incorporated by reference herein for all purposes.

It may be desirable to improve the current state of the art by providing a device for thermally controlling an electrosurgical instrument. That is, it may be desirable to cool the one or more return electrodes and/or the effector without increasing a section size or weight of the electrosurgical instrument and/or the effector and without increasing the cost and/or the complexity thereof.

SUMMARY

An effector is provided that includes a tubular body having a proximal end and a distal end. The effector includes a plug at the distal end of the tubular body; an active electrode provided at the distal end of the body; an insulator on the body; and one or more return electrodes on the insulator. The body dissipates heat generated by the one or more return electrodes from the distal end of the body to the proximal end of the body.

An effector is provided that includes a body, a plug, an active electrode, an insulator on the body, and one or more return electrodes. The body has an interior portion, a proximal end, and a distal end. The plug is located at the distal end of the body. The active electrode in communication with the plug. The one or more return electrodes located on the insulator. The body dissipates heat from the distal end of the body to the proximal end of the body. The one or more return electrodes are vapor deposited onto the insulator.

A method of making an effector is also provided. The method includes steps of: providing an insulator over at least a portion of a tubular body having a proximal end and a distal end; providing a plug at the distal end of the body and providing an active electrode in communication with the plug and extending from the distal end of the body. The method also includes steps of insulating at least a portion of the body with an insulator; and providing one or more electrodes on the insulator.

DETAILED DESCRIPTION

Figure 1A:
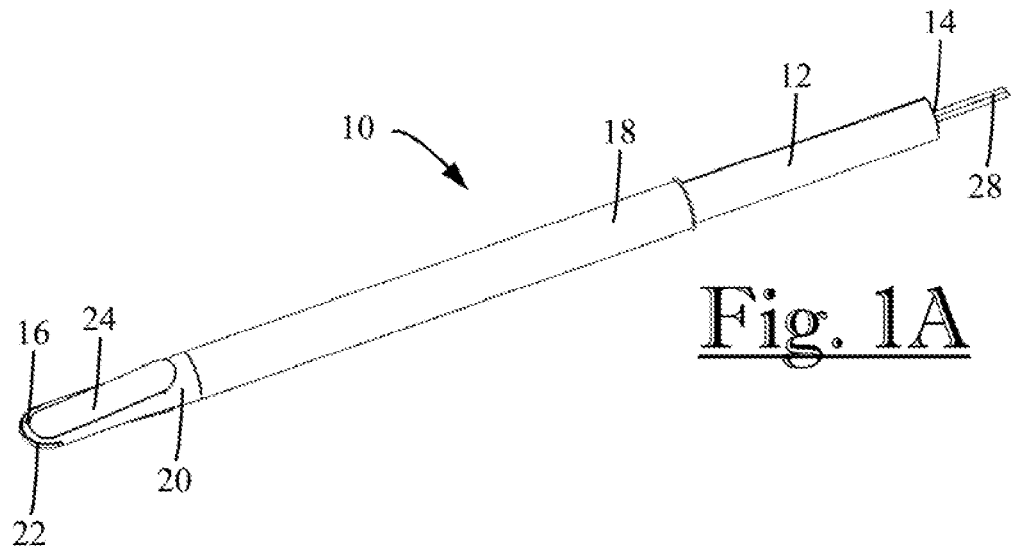
FIG. 1A is a perspective view of an effector.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present disclosure provides one or more effectors. The one or more effectors may be any device, instrument, or component thereof that is adapted to effect or treat an object or anatomical feature of interest. For example, the effector can be used to move, grip, grasp, capture, compress, push, pull, cut, coagulate, weld, seal, dissect fulgurate, perform hemostasis, and/or otherwise effect an object or anatomical feature such as a vessel, tissue, artery, vein, organ, skin, the like, or a combination thereof. The one or more effectors can be used in virtually any medical procedure. For example, the effector can be used in open procedures, laparoscopic procedures, minimally invasive procedures, electrosurgical procedures, or a combination thereof.

One or more instruments can comprise one or more of the effectors. The one or more instruments can be used in medical procedures, in non-medical procedures, or both. Exemplary instruments include forceps, tweezers, a dissector, scissors, a scalpel, a spatula, a hook, J-hook, or a combination thereof. The effector can be included in a combo device. For example, the effector can be a central component located between opposing arms, and can function as a monopolar blade electrode, a bipolar blade electrode, or both. In such a configuration, the arms of the combo device need not include electrodes, thus resulting in a less-expensive and less-complicated construction. That is, the arms of the combo device can function as gripping or grasping arms. The one or more instruments, effectors, or both may be fully and/or partially disposable, reusable, reposable, or a combination thereof.

The instrument may be a forceps. The forceps may include at least two arms, a blade electrode, or a combination of both. The arms may be any part that may be used to grip, hold, squeeze, surgically effect, or a combination thereof an object or anatomical feature. The arms may include one or more gripping features that may assist in gripping, holding, squeezing, or a combination thereof an object or anatomical feature. One or both of the arms may be movable. One or both of the arms may be longitudinally static and moveable relative to each other. Preferably, at least one of the arms is both longitudinally movable (e.g., movable along the length of the hand piece) and laterally movable (e.g., movable towards and away from an opposing arm). The arms may be selectively retractable and/or extendable so that one or more tip regions are exposed. The arms, the blade electrode, or a combination thereof may be or may include one or more of the effectors disclosed herein. The arms, the blade electrode, or a combination thereof may include the effector, the one or more electrodes, or both. The effector, the arms, the blade electrode, or a combination thereof may include a tip region. The tip region may include a portion that is configured to assist in facilitating gripping, holding, squeezing, transferring of a therapy current, or a combination thereof. The lip region may be located at a distal end of the effector, arms, blade electrode, or a combination thereof. The tip region may include teeth, serrations, mouse teeth, be free of teeth (i.e., smooth), or a combination thereof. The tip region may include the effector, the one or more electrodes, or a combination thereof.

The one or more effectors, instruments, or both can be used with or without power. When used with power, the one or more effectors, instruments, electrodes, or a combination thereof can supply one or more electrical currents, therapies, and/or signals. When used with power, the one or more effectors, instruments, electrodes, or a combination thereof can supply electrical energy, ultrasonic energy, heat energy, RF energy, or a combination thereof to treat or effect an object or anatomical feature. The one or more effectors or instruments can be used with monopolar energy, bipolar energy, a blended energy comprising monopolar and bipolar energy, or a combination thereof. During use, the energy, current, therapy, and/or signal may be passed from, through, or between the effector, the one or more electrodes, a remote pad, a patient or anatomy, or a combination thereof to electrically effect an object or anatomical feature. Electrically effect an object or anatomical feature may include cutting, dissecting, coagulating, welding, sealing, fulgurating, performing hemostasis, etc.

The one or more effectors, instruments, or both can be used in a monopolar mode, a bipolar mode, or both. The one or more effectors, instruments, or both can be switched between the monopolar mode and the bipolar mode by closing one or more activation circuits. Switching between the monopolar mode and the bipolar mode may be done by manipulating one or more user inputs on the hand piece of the instrument, at a remote location (e.g., a foot pad), or a combination thereof. Switching between the monopolar mode and the bipolar mode limy be done at a surgical site without having to remove the instrument from the surgical site or swap the instrument with another instrument.

In the monopolar mode, one or more electrical energies, currents, therapies, and/or signals may be passed from one pole or electrode(s) of the in effector, or both, to or through an object or anatomical feature, to another pole or electrode(s) located at a remote location such as a remote pad or patient pad. The electrical energy, current, therapy and/or signal can be passed to or through the object or anatomy to cut, dissect, coagulate, fulgurate, weld, seal, perform hemostasis, etc. on the object or anatomy.

In the bipolar mode, one or more suitable electrical energies, currents, therapies, and/or signals may be passed from a pole or electrode(s) located on the effector, instrument, or both to or through an object or anatomical feature, to another pole or electrode(s) located on the effector, instrument, or both. The electrical energy, current, therapy and/or signal can be passed to or through the object or anatomy to cut, dissect, coagulate, fulgurate, weld, seal, perform hemostasis, etc. on the object or anatomy.

In the bipolar mode, the instrument, effector, or both can be selected or switched to operate in a first bipolar electrical mode, a second bipolar electrical mode, and a third bipolar electrical mode.

In the first bipolar electrical mode, one or more electrical energies, currents, therapies, and/or signals can be passed to or through an object or anatomical feature from one or more active electrodes to one or more return electrodes.

In the second bipolar electrical mode, the one or more active electrodes may be dormant and one or more electrical energies, currents, therapies, and/or signals can be passed to or through an object or anatomical feature between the one or more return electrodes.

In the third bipolar electrical mode, the instrument, effector, or both can be modulated or switched between the first bipolar electrical mode and the second bipolar electrical mode. That is, for a selected period of time, the electrical energies, currents, therapies, and/or signals are passed to or through an object or anatomical feature from one or more active electrodes to one or more return electrodes. Then for another period of time, the electrical energies, currents, therapies, and/or signals are passed to or through an object or anatomical feature between the one or more return electrodes. In the third bipolar electrical mode, a user may be able to select the amount of time each of the modes operate or could be automatically controlled by the power source logic based on feedback. In the third bipolar electrical mode, the modulation or switching can be automatically controlled, manually controlled, or both.

The one or more electrical energies, currents, therapies, and/or signals can be supplied to the one or more electrodes, effectors, instruments, or a combination thereof by one or more suitable sources. An example of a suitable source is a generator. The source or generator may supply electrical energy, ultrasonic energy, heat energy, RF energy, or a combination thereof. The source or generator may include one or more power connections. The power connections may be any port or connection on the source or generator that one or more power connectors, leads, or wire from the instrument or effector may be plugged into so that the one or more electrical energies, currents, therapies, and/or signals can be supplied to the electrodes, instrument, effector, or a combination thereof. The source or generator may include a central processing unit (CPU). The source, generator, CPU, or a combination thereof may be used to switch the electrodes, effector, the instrument, or a combination thereof to operate in the monopolar mode, the bipolar mode, the first bipolar electrical mode, the bipolar second electrical mode, the third bipolar electrical mode, or any combination thereof.

The one or more effectors can include one or more bodies. The body may function to provide structure for the effector. The body may function to dissipate heat or transfer heat from a region having a greater concentration of heat to a region having a lower concentration of heat. For example, the body may dissipate heat or transfer heat from a distal end of the effector or body to a proximal end of the effector or body a central portion of the effector or body to a proximal end of the effector or body; or a combination thereof. For example, the body may dissipate heat air transfer heat from the one or more return electrodes so that the return electrodes do not overheat or get too hot. For example, the body may dissipate heat or transfer heat from the one or more active electrodes so that the active electrodes do not overheat or get too hot. The body may be electrically connected to the generator and may function to electrically power the one or more active electrodes.

The body may be a member extending between a proximal end and a distal end. The body may be an elongated member. The body may be substantially straight, or may include one or more bends, turns, and/or arcs. The body may be substantially rigid. The body may include one or more portions that are substantially flexible and/or resilient. The body may be tubular, hollow, solid, or may include portions that are hollow and solid. The body may include a generally constant, uniform cross section, or the cross section may change or vary along a length thereof. The body can have one or more open ends. One or both of the open ends of the body can be closed by either squeezing or crimping the ends; scaling the ends with solder or welding; plugging the ends with one or more plugs or closures; or a combination thereof. The plug can be a closed ended tube that is closed by squeezing, crimping, sealing with solder or welding, or a combination thereof. The body may have a wall thickness on the order of approximately 0.20 mm or more, 0.30 mm or more, 0.40 mm or more, 0.50 mm or more 0.60 mm or more, 0.70 mm or more, 0.75 mm or more, or even 0.80 mm or more. The body may have a wall thickness on the order of approximately 1.00 mm or less, 0.90 mm or less, 0.80 mm or less. Preferably, the body has a thickness on the order of approximately 0.75 mm.

The body may be made from any suitable material. Preferably, the body is made from a material suitable for use in medical procedures. Preferably, the body is made from a material with good thermal conduction properties, thermal dissipation properties, or both. For example, the body may comprise as heat pipe, a heat tube, copper, silver, aluminum, gold, graphene formed into rods, graphene formed into ropes, steel, carbon, a material with high thermal dissipation, or a combination thereof.

The body may comprise one or more heat pipes, one or more heat tubes, one or more central heat dissipators, or a combination thereof. The one or more heat pipes, heat tubes, or central heat dissipators may function to dissipate or transfer heat from a region having a greater concentration of heat to a region having a lower concentration of heat. For example, the one or more heat pipes, heat tubes, or central heat dissipators may dissipate or transfer heat from a distal end of the effector or body to a proximal end of the effector or body; a central portion of the effector or body to a proximal end of the effector or body; or a combination thereof. For example, the one or more heat pipes, heat tubes, or central heat dissipators may dissipate heat or transfer heat from the one or more return electrodes so that the return electrodes do not overheat or get too hot. It may be desirable to transfer heat from the one or more return electrodes so that an object or anatomical feature does not stick or burn to the return electrodes; so that the return electrodes do not become the active electrodes, or a combination thereof. It is contemplated that during use, preferably, the active electrode will be hotter than the return electrodes. It is contemplated that it is preferable for the active electrode to get hot, particularly at the distal tip.

A heat pipe may be defined as a heat transfer unit, a solid state dissipator, piece of material that can transfer heat readily, and/or may be a vacuum containing fluid that moves to create a cooling effect. The central heat dissipater, heat tube, or both may be sealed, may be self-contained, and may include a vacuum, or a combination thereof so that additional fluid is not needed to perform a cooling function, similar to a heat pipe. The heat pipe may include a suitable fluid to absorb heat, remove heat, dissipate heat, or a combination thereof. For example, the heat pipe may be filled with water, alcohol, sodium, ammonia, ethanol, methanol, or a combination thereof. The fluid may undergo one or more phase changes, and preferably two or more phase changes (e.g., evaporation, condensation, or both) that assist in removing heat from the one or more electrodes, the body, the effector, or a combination thereof.

The one or more heat pipes may be sufficiently long and/or have a sufficiently large cross-sectional thickness (e.g., diameter) so that fluid may travel from the distal end of the heat pipe to the proximal end of the heat pipe so that the fluid is cooled. The one or more heat pipes may be sufficiently long and/or have a sufficient cross-sectional thickness so that evaporated fluid can travel from the hot end of the beat pipe (e.g., distal end) to the cool end of the heat pipe (e.g., proximal end) where the fluid condenses. During use, when the electrodes at the distal end of the body or heat pipe are heated, the fluid within the body or heat pipe may be heated. The heated fluid may then evaporate. The evaporated fluid may move from the distal end of the heat pipe or body to the proximal end where the heated fluid may condense and release the heat. The condensate may then move from the proximal end back to the distal end and the cycle repeats. The fluid, when condensed, may travel from the cool end to the hot end via capillary action, gravity, or combination thereof. The ends of the one or more bodies or heat pipes may be closed by either squeezing and sealing it with solder or plugging the ends with one or more plugs.

The one or more effectors, bodies, or both may include one or more plugs or closures. The one or more plugs or closures may be a closing that may or may not be hermetically sealed. The one or more plugs or closures may be a crimped section which may include solder. The one or more plugs may function to seal or cap one or more ends of the body, the heat pipe, or both. The one or more plugs may function to be used to affect an object or anatomical feature. The one or more plugs may also incorporate steel, copper, silver, aluminum, graphene, gold, carbon, or another material that is known to improve cut performance of the device tip, or a combination thereof. The one or more plugs may be equipped with a coating shim that minimizes heat transfer into the plug. The one or more, plugs may be formed from a suitable material that has poor thermal conduction so that heat from the cut element of the plug, the active electrode, or both is not transferred, dissipated, or lost via the thermally conductive heat pipe, body, or both. The one or more plugs may be formed from a suitable material that has poor thermal conduction so that heat from the plug, the active electrode, or both is not transferred to the insulator, the body, the heat pipe, or a combination thereof. The one or more plugs may be formed from a suitable material that has poor thermal conduction so that the one or more active electrodes in communication with the plug get hot first and function as the active electrode and maintain the heat. The one or more plugs may be at least partially inserted into an inner portion of the body, heat pipe, or both. The one or more plugs may be press-fit into the distal opening of the body, the heat pipe, or both, and/or may be secured thereto with a suitable mechanical fastener, an adhesive, welding, soldering, or a combination thereof. The one or more plugs may receive at least a portion of a blade, an active electrode, or both. The one or more blades, active electrodes, or both may be embedded in the plug. The one or more plugs may be an active electrode. The one or more plugs or closures may contain, receive, or be one or more return electrodes. The one or more plugs may be in communication with a source of energy such as a generator. At least a portion of the plug, a portion of the blade, or both can be coated with the insulator so that the active electrode, the plug, or both are separated from the return electrodes.

The one or more effectors, bodies, or both may include one or more insulators. The insulator may coat at least a portion of the effector, body, plug, or as combination thereof. For example, the distal end of the effector, the plug, or both may include the insulator. The insulator may function to electrically separate the active electrodes and the plugs from the return electrodes. The insulator may function as a thermal conductor so that heat from the one or more return electrodes can be transferred or dissipated to the body, heat pipe, or both.

The one or more insulators may comprise any suitable material. Preferably, the insulator comprises a material having good dielectric strength, arc resistance, or both. For example, the insulator may comprise a material that has a dielectric strength on the order of approximately 1 ac-kV/mm or more, 5 ac-kV/mm or more, 10 ac-kV/mm or more, 15 ac-kV/mm or more, 20 ac-kV/mm or more, 50 ac-kV/mm or more, 75 ac-kV/mm or more, 90 ac-kV/mm or more or even 95 ac-kV/mm or more. The insulator may comprise a material that has a dielectric strength on the order of approximately 200 ac-kV/mm or less ac, 100 ac-kV/mm or less, 97 ac-kV/mm or less, 50 ac-kV/mm or less, 25 ac-kV/mm or less, 20 ac-kV/mm or less, 18 ac-kV/mm or less, 16 ac-kV/mm or less, 15 ac-kV/mm or less, 10 ac-kV/mm or less, 8 ac-kV/mm or less, 7 ac-kV/mm or less. The insulator may include a material having good thermal transfer properties. For example, the insulator may comprise a material that has a thermal conductivity of 1 W/m° K or more, 2 W/m° K or more, 5 W/m° K or more, 15 W/m° K or more, 20 W/m° K or more, 30 W/m° K or more, 50 W/m° K or more, 75 W/m° K or more, 100 W/m° K or more, 125 W/m° K or more, or even 130 W/m° K or more. The thermal conductively of the insulator may be on the order of 200 W/m° K or less, 175 W/m° K or less, 150 W/m° K or less, 140 W/m° K, 100 W/m° K or less, 60 W/m° K or less, 50 W/m° K or less, 35 W/m° K or less, 32 W/m° K or less, 5 W/m° K or less, or 3 W/m° K or less.

The insulator may be thin enough to optimize the thermal conduction, but thick enough to provide electrical insulation from the one or more electrodes. For example, the insulator may have a thickness on the order of approximately 0.001 mm or more, 0.01 mm or more, 0.02 mm or more, 0.03 mm or more, 0.04 mm or more, 0.05 mm or more, 0.06 mm or more, 0.07 mm or more, 0.08 mm of more, 0.09 mm or more, 0.10 mm or more 0.15 mm or more, 0.16 mm or more, or even 0.20 mm or more.

If a ceramic is used for the insulator, an Alumina based material may be preferred over a Silicon Nitride version because Alumina may have better thermal conductivity than Silicon Nitrade. Exemplary insulators may include silicone or polytetrafluoroethylene (PTFE), Aluminum Nitride, Aluminum Oxide, Silicon Nitride, Zirconium Oxide MgO stabilized, Boron Nitride, Yttria stabilized Zirconia, diamond like carbon (DLC), or a combination thereof.

The one or more insulators can be applied to the body or heat pipe via any suitable methods. For example, the insulator can be a coating or spray on the body or heat pipe. Preferably, the one or more insulators are applied to the body, heat pipe, or both such that little or no gaps (e.g., air gaps) are between the insulator and the both or the heat pipe. An air gap may function as a thermal barrier between the insulator and the heat pipe or body and prevent heat from the return electrodes from being properly and efficiently transferred or dissipated via the body, the heat pipe, or both.

The one or more effectors, bodies, or both may include one or more electrodes. The electrodes may function to pass, transfer, grad or receive one or more electrical energies, currents, therapies, and/or signals. The one or more electrodes may function to pass one or more electrical currents, therapies, and/or signals to or through one or more objects, anatomical features, or both. The one or more electrodes may include materials that are good electrical conductors. For example, the one or more electrodes may comprise steel, copper, iron, nickel, tungsten, steel, stainless steel, surgical steel, copper, titanium nitride, or a combination thereof. The one or more electrodes may be coated with a material that conducts electricity.

The one or more electrodes may be electrically connected to one or more generators or other sources of energy. The one or more electrodes may be electrically connected to one or more generators or sources of energy via any suitable manner. For example, one or more wires, traces, or conductors can connect the electrodes to lead wires from the generator. The body may function to electrically connect the one or more active electrodes to the generator.

The one or more electrodes may comprise one or more active electrodes and one or more return electrodes. The one or more active electrodes may function to pass, transfer, and/or deliver the one or more electrical energies, currents, therapies, and/or signals to the object, anatomical feature, the one or more return electrodes, or a combination thereof. Preferably, the one or more active electrodes comprise a material that retains heat, has a low thermal conductivity, or both. The one or more active electrodes may be positioned at a distal end or tip of the effector, body, heat pipe, heat tube, central heat dissipater, or combination thereof. For example, in some configurations, it may be preferred for the active electrode or blade be positioned as far away from the body or heat pipe as possible. This may be desirable in monopolar uses where voltages are much larger, which tends to heat the active electrode more. Accordingly, in monopolar uses, it may be desirable to prevent the heat from the active electrode from transferring or conducting to the body or heat pipe so that the return electrodes are not heated and/or so that the body or heat pipe can be reserved for cooling only the return electrodes. The one or more active electrodes may be in communication or extend from one or more plugs in the body, heat pipe or both. The one or more active electrodes may have any shape. The active electrode may include a blade. The effector may include any size and any number of active electrodes. Preferably, the size and number of active electrodes is less than the size and number of return electrodes.

The one or more return electrodes may function to provide a return path for the one or more electrical currents, therapies, and/or signals. Preferably, the one or more return electrodes are spaced apart from the one or more active electrodes. The one or more return electrodes may be provided on the insulator. The one or more electrodes may be attached to or formed on the body in any suitable way. For example, the one or more return electrodes may be printed, screen printed, ink-jet printed, etched, soldered, stamped, sprayed, formed in metallized tracks, or vapor deposited onto the body, the insulator, or both. Preferably, the one or more return electrodes are deposited onto the body, the insulator, or both such that little or no gaps (e.g., air gaps) are located between the return electrodes and the body, the insulator, or both. An air gap may function as a thermal barrier between the return electrode and the insulator, body, or both and prevent heat from the return electrodes from being properly and efficiently transferred or dissipated via the body, the heat pipe, or both.

The effector may include any size and any number of return electrodes. Preferably, the size and number of return electrodes is more than the size and number of active electrodes. For example, the effector may include two or more return electrodes, three or more return electrodes, four or more return electrodes. In some configurations, the effector may include two return electrodes—one return electrode on each side or surface of the effector or tip. In other configurations, the effector may include four return electrodes—two return electrodes on each side or surface of the effector or tip.

The effector may comprise one or more blades. The one or more blades may be made of steel or other material that has poor thermal conduction so that the one or more blades get hotter faster and acts as the one or more active electrodes. The one or more blades may have any suitable shape so that the effector or medical instrument can be used as a spatula, hook, a knife, or a combination thereof. The one or more blades may be moveable relative to a distal end of the body, heat pipe or both so that the blade can be positioned away from the body in some configurations and close to the body in other configurations. For example, in some configurations, it may be preferred for the blade to be positioned further from the body or heat pipe so that heat from the blade can be prevented from transferring or conducting to the body or heat pipe. Accordingly, moving the blade away from the body in some configurations may prevent the return electrodes from heating.

The effector may include one or more heat sinks. The one or more heat sinks may be connected to the one or more bodies, heat pipes, or both. Each body, heat pipe, or both may be connected to a heat sink, have an integral heat sink, or both. The bodies, heat pipes, or both may extend through the heat sinks and the heat sinks may remove heat therefrom through thermal contact. The body, heat pipe, or both may transfer heat to the heat sink via a heat transfer medium (e.g., a thermal paste) so that heat is transferred from the body, heat pipe or both to the heat sink. The heat sink and the heat pipes may be made of the same material. The heat sink may be an extended portion of the body, heat pipe, or both that acts to dissipate heat. For example a coil or other extended shape may extend from an end of the body, heat pipe, or both and may allow for heat transfer. The heat sink may be located on the cold end, of the body, heat pipe, or both, on the proximal end of the body, heat pipe, or both, or a combination thereof. The heat sink may increase the surface area of each of the one or more heat pipes, bodies, or both. The heat sink may be partially and or entirely shielded from contact by the user so that heat from the body, heat pipe, the heat sink, or a combination thereof does not directly contact the user. The heat sink may be made of a material with high conductivity, higher conductivity than the heat pipe, or both. The heat sink may use natural convection, forced convection, or both to dissipate heat. The heat sink may include one or more heat exchange surfaces that dissipate heat from the fluid. The one or more heat exchange surfaces may increase the surface area of the heat exchanger relative to the body, heat pipe, or both, so that heat is dissipated. The surface area of the heat exchange surface may be about two times or more, about three times or more, or even about four times or more than the surface area of the body, heat pipe, or both. The one or more heat exchange surfaces may be and/or include fins, baffles, an increase in surface area, tubes, plates, ribs, or a combination thereof.

The effector may include one or more fluid evacuation conduits. The one or more fluid evacuation conduits may function to remove smoke and/or air during an electrosurgical procedure. The fluid evacuation conduits may function to draw air from a point of interest so that at least localized air movement is created. The fluid evacuation conduit may function to circulate air around an electrosurgical instrument so that the instrument is cooled. The fluid evacuation conduits may be an integral part of the body, the heat pipe, or both. The fluid evacuation conduits may be in communication with the blade electrode. The fluid evacuation conduit may be connected to the body, the heat pipe, or both so that an is removed from a region proximate to the distal end of the effector, instrument, or both during performance of a surgical procedure. The one or more fluid evacuation conduits may move a sufficient amount of air so that a majority (i.e. 50 percent or more, 60 percent or more, 75 percent or more, or even 90 percent or more) of the smoke is removed from the distal end of the effector, the instrument, or both as the smoke is created. Each of the one or more fluid evacuation conduits may move about 0.03 m$^3$/min or more, about 0.15 m$^3$/min or more, about 0.3 m$^3$/min or more, or even about 0.75 m$^3$/min or more. The fluid evacuation conduits may be on all time the electrosurgical instrument is connected to a power source, a vacuum source, or both. The fluid evacuation conduits may turn on only when a therapy current or energy is being applied. The one or more fluid evacuation conduits may be statically located on the effector. The fluid evacuation conduits may be movable on the instrument so that the fluid evacuation conduit may be moved to a location of smoke creation. The fluid evacuation conduit may be a series of holes in a tip region of the body heat pipe, or both. The fluid evacuation conduit may be a series of holes along a length of the heat pipe, body, or both. Preferably, the fluid evacuation conduit is connected to the effector and is movable with the body when the effector is moved.

Figure 1B:
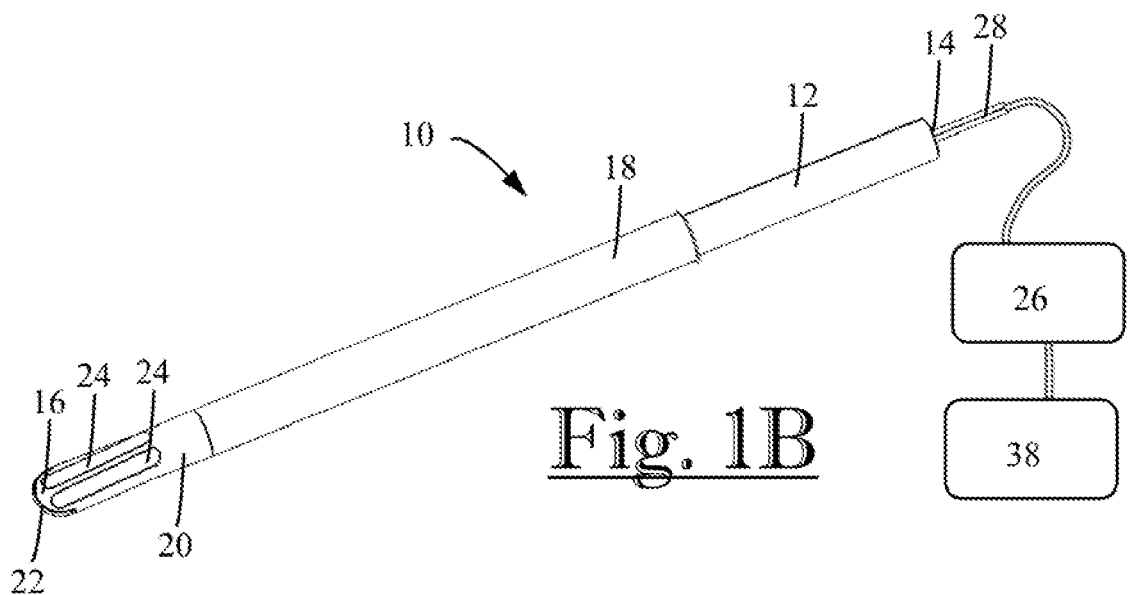
FIG. 1B is a perspective view of an effector.

FIGS. 1A and 1B illustrate an exemplary effector 10. The effector 10 includes a body 12 extending between a proximal end 14 and a distal end 16. The effector 10 includes an insulator 18, and a tip portion 20 comprising an active electrode 22 and return electrodes 24. The effector 10, the one or more of the electrodes 22, 24, or a combination thereof are in communication with a generator 26 is leads 28. Leads can also connect the effector 10, the one or more of the electrodes 22, 24, the generator 26, or a combination thereof to a remote pad or patient pad 38.

Figure 2:
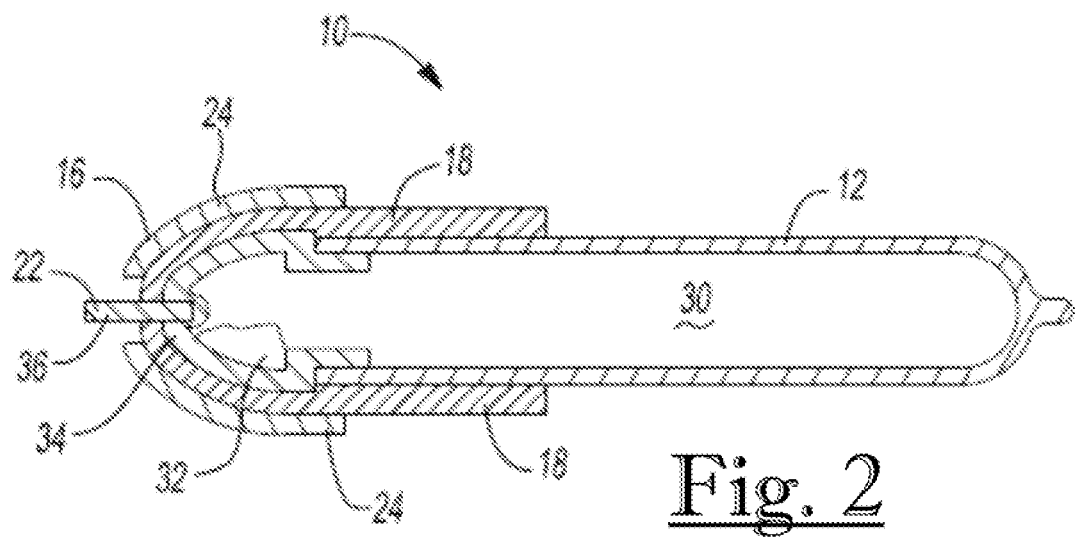
FIG. 2 is as cross-sectional view of an effector.

FIG. 2 illustrates a cross section of an exemplary effector 10. In some configurations, an interior portion 30 of the body 12 includes a heat transfer fluid 32. The effector 10 includes an insulator 18 and return electrodes 24. The effector 10 includes a plug 34 extending from a distal end 16 of the body 12. The active electrode 22 is in communication with the plug 34. The active electrode 22 may be a blade 36.

Figure 3:
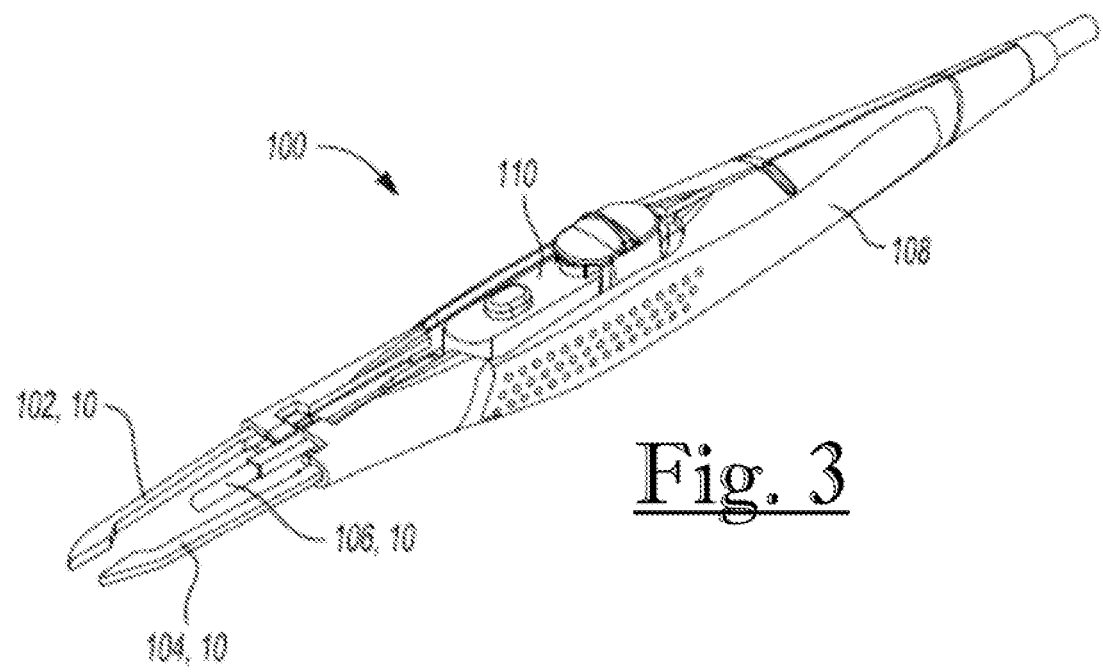
FIG. 3 is a perspective view of an instrument including an effector.

FIG. 3 illustrates an exemplary instrument 100 that is a forceps. The instrument 100 includes a first arm 102, a second arm 104, and a blade 106. One or more of the first arm 102, the second arm 104, and the blade 106 comprise the effector 10. The blade 106 may be a blade electrode.

The instrument 100 includes a handle 108 with controls 110 for manipulating and switching the instrument 100 to operate in a monopolar mode, a bipolar mode, a first bipolar electrical mode, a bipolar second electrical mode, a third bipolar electrical mode, or any combination thereof.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 4 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. An effector comprising:
    i. a body having a proximal end and a distal end;
    ii. a plug at the distal end of the tubular body;
    iii. an active electrode extending from the plug;
    iv. an insulator on the body; and
    v. one or more return electrodes on the insulator;
    wherein the body dissipates heat generated by the one or more return electrodes from the distal end of the body to the proximal end of the body, and
    wherein the distal end of the body is plugged with the plug and crimped.

2. The effector of claim 1, wherein the body comprises a copper tube, a heat pipe, or both.

3. The effector of claim 2, wherein at least a portion of the plug is coated with the insulator.

4. The effector of claim 1, wherein the one or more return electrodes are vapor deposited onto the insulator.

5. The effector of claim 1, wherein the active electrode is made of steel and the plug contains conductive material.

6. The effector of claim 1, wherein the one or more return electrodes comprise a plurality of the return electrodes, wherein the body includes a tip portion comprising an upper surface having one of the return electrodes and a lower surface having another one of the return electrodes.

7. The effector of claim 1, wherein the one or more return electrodes comprise a plurality of the return electrodes, wherein the body includes a tip portion comprising an upper surface having two return electrodes and a lower surface having another two return electrodes.

8. A forceps comprising the effector of claim 1, wherein the effector is a blade electrode.

9. An electrosurgical instrument comprising the effector of claim 1, wherein the electrosurgical instrument is operable in a bipolar mode,
    wherein the one or more return electrodes comprise a plurality of the return electrodes,
    wherein in the bipolar mode, the electrosurgical instrument is switchable between a first bipolar electrical mode and a second bipolar electrosurgical mode, and wherein in the first bipolar electrical mode a first therapy current is provided to anatomy from the active electrode to at least one of the return electrodes and in the second bipolar electrosurgical mode a second therapy current is provided to the anatomy between two or more of the return electrodes.

10. The effector of claim 1, wherein the plug is at least partially inserted into an inner portion of the body.

11. The effector of claim 1, wherein the active electrode is a blade.

12. The effector of claim 1, wherein at least a portion of the plug is coated with the insulator.

13. The effector of claim 1, wherein the plug is formed from a material so that heat from the active electrode is not transferred to the body.

14. The effector of claim 1, wherein the active electrode extends distally from a distal-most end of the body.

15. A method of making an effector comprising the steps of:
   i. providing an insulator over at least a portion of a tubular body having a proximal end and a distal end;
   ii. providing a plug or closure at the distal end of the body;
   iii. providing an active electrode in communication with the plug and extending from the distal end of the body; and
   iv. providing one or more return electrodes on the insulator.

16. The method of claim 15, wherein the one or more return electrodes comprise a plurality of the return electrodes, wherein the method includes one or more steps of connecting the effector to a generator so that:
   a. a therapy current can be passed between the active electrode and a remote pad;
   b. a therapy current can be passed between the active electrode and one of the return electrodes; and/or
   c. a therapy current can be passed between two or more of the return electrodes.

17. The method of claim 15, wherein the method includes a step of at least partially inserting the plug into an inner portion of the body.

18. An effector comprising:
   i. a body having a proximal end and a distal end;
   ii. a plug distally extending from the distal end of the body, the plug is at least partially received into an inner portion of the body;
   iii. an active electrode extending distally from a distal end of the plug;
   iv. an insulator located on at least a portion of the body and on at least a portion of the plug; and
   v. one or more return electrodes located on the insulator;
   wherein the body is configured to dissipate heat generated by the one or more return electrodes from the distal end of the body to the proximal end of the body.

19. The effector of claim 18, wherein the body is a heat pipe.

20. The effector of claim 18, wherein a material of the body is different than a material of the plug.

* * * * *